United States Patent [19]

Farcasiu

[11] 4,406,821
[45] Sep. 27, 1983

[54] ETHERIFICATION CATALYST
[75] Inventor: Dan Farcasiu, Princeton, N.J.
[73] Assignee: Exxon Research and Engineering Co., Florham Park, N.J.
[21] Appl. No.: 412,784
[22] Filed: Aug. 30, 1982
[51] Int. Cl.³ .............................................. B01J 27/02
[52] U.S. Cl. ................................................... 252/440
[58] Field of Search ........................................ 252/440
[56] References Cited

U.S. PATENT DOCUMENTS 3,119,875  1/1964  Steinmetz et al. .............. 252/440 X
3,737,445  6/1973  Dodman et al. ................. 252/440 X

FOREIGN PATENT DOCUMENTS 332756   7/1930  United Kingdom .
600837   4/1948  United Kingdom .
1488325 10/1977  United Kingdom .

OTHER PUBLICATIONS

Alkylation of Phenols on $Fe_2O_3$ and $Cr_2$ (Inoue and Enomoto) Chem. Pharm, Bull., 24(9)2199–2203 (1976).

Primary Examiner—Delbert E. Gantz
Assistant Examiner—William G. Wright
Attorney, Agent, or Firm—Edward M. Corcoran

[57] ABSTRACT

An etherification catalyst comprising a sulfated composite of one or more transition metal oxides on alumina. The catalysts of this invention may be used to etherify phenols. Preferred metal oxides are oxides of tungsten, hafnium, and mixtures thereof.

15 Claims, No Drawings

ETHERIFICATION CATALYST

BACKGROUND OF THE INVENTION

1. Field of the Invention

This invention relates to a catalyst useful for etherifying phenols. More particularly, this invention relates to a catalyst useful for etherifying phenols which comprises a sulfated composite of one or more transition metal oxides supported on alumina.

2. Background of the Disclosure

The catalytic etherification or alkylation of phenols with low molecular weight alkyl alcohols, such as the methylation of phenol to anisole with methanol is well-known in the art. For example, British Pat. No. 600,837 discloses the formation of anisole over an activated alumina catalyst while British Pat. No. 1,488,325 shows anisole production over either an eta or gamma alumina catalyst. Inoue and Enomoto teach the alkylation of phenols with methanol over ferric oxide and chromic oxide catalysts (Inoue and Enomoto, ALKYLATION OF PHENOLS ON $Fe_2O_3$ and $Cr_2O_3$, Chem. Pharm. Bull., 24(9)2199–2203(1976). However, the selectivity and stability of these catalysts is not adequate enough for commercial use. It is well-known that the catalytic methylation of phenol produces coke which rapidly deactivates the catalyst and the catalyst then has to be regenerated. As a practical matter, these prior art catalysts cannot be regenerated due to their instability under regenerating conditions.

A particularly significant application for the etherification of phenols and cresols resides in the synthetic fuels area, such as raw or untreated naphtha fractions or feeds derived from the liquefaction of coal. The aromatic hydroxyl compounds, such as phenol, cresols, and their homologues, present in raw coal naphtha contribute to its instability and also tend to poison catalysts used to reform these naphthas to increase their octane value. Before raw coal naphtha can be reformed to increase its octane value, it must be hydrorefined or refined with hydrogen to eliminate sulfur and nitrogen compounds present therein which would otherwise poison the reforming catalyst. If phenols are present in the raw naphtha during the hydrorefining operation, the oxygen present in the phenolic hydroxyl groups results in a hydrogen debit with no significant increase in the octane value of the naphtha. On the other hand, the corresponding alkyl and aryl ethers of phenol or phenols, such as anisole, are useful blending agents for improving the octane value of coal-derived naphthas. Therefore, it would be a significant improvement to the art if one could etherify the phenols derived from such naphthas and, more preferably, if such etherification could be accomplished without having first to remove the phenols from the raw naphtha. However, any catalyst useful for etherifying the phenols in or derived from coal liquids must be resistant to poisoning deactivation and must also be capable of being successfully regenerated without appreciable loss of catalytic activity.

Those skilled in the art also know that, the etherification of phenols with alcohols is normally accompanied by the alkylation of the aromatic ring. Although the main product of ring methylation of phenol by methanol is ortho-cresol, the formation of 2,6-xylenol, is also possible. These ring methylated products have all the undesirable properties of phenol with respect to poisoning reforming catalysts, etc. Therefore, a good etherification catalyst should be more selective to oxygen methylation than to ring methylation. This preferred selectivity may be defined as the ratio of the yield of ether products to the yield of all alkylated products. If the process is limited to monomethylation, the selectivity to anisole for the methylation of the parent phenol is defined as the yield of anisole divided by the yield of anisole plus cresols.

SUMMARY OF THE INVENTION

It has now been discovered that phenols can be etherified by contacting, at elevated temperature, a phenol feed with a reactant selected from the group consisting essentially of alcohols, ethers and mixtures thereof in the presence of an acid catalyst comprising a sulfated composite of at least one transition metal oxide selected from the group consisting essentially of oxides of W, Hf, Nb, Ta, Zr and mixtures thereof, supported on a high surface alumina support, said contacting occuring for a time sufficient to convert at least a portion of said phenol to its corresponding ether with said reactant. Tungsten and hafnium oxides and their mixtures are particularly preferred as the catalytic transition metal oxides. By elevated temperature is meant a temperature high enough to maintain the reactants in the vapor phase to insure that the etherification reaction occurs in the gas phase which, in general, will be at least about 200° C.

It has been found that sulfating the composite produces a catalyst with greater selectivity towards the production of anisole than if the catalyst had not been sulfated. By sulfated is meant that the catalyst composite is treated with a suitable sulfating agent such as an aqueous solution of $H_2SO_4$ and then calcined to produce the catalyst of this invention.

DETAILED DESCRIPTION

As hereinbefore stated, the catalysts of this invention will comprise a composite of the oxides of one or more transition metals selected from the group consisting of tungsten, hafnium, zirconium, tantalum, niobium and mixtures thereof supported on a relatively high surface area alumina support, said composite being sulfated and then calcined to form the catalyst of this invention. Oxides of tungsten, hafnium, and mixtures thereof are particularly preferred. By high surface area alumina support is meant a support comprising alumina which has a surface area of at least 30 $M^2/g$, preferably about 50 $M^2/g$ and still more preferably at least about 100 $M^2/g$ as measured by the Brunauer Emmett-Teller (BET) method. Gamma alumina is particularly preferred, although other forms of alumina as well as mixtures of silica and alumina may also be used as the support. The transition metal oxide-alumina support composite will be sulfated with a suitable sulfating agent such as $H_2SO_4$. Following the sulfating treatment, the sulfated catalyst composite will then be calcined at a temperature of from about 300° to 700° C., preferably 400° to 600° C. in air or other oxygen-containing atmosphere, as long as the atmosphere is net oxidizing to form the catalyst of this invention.

The transition metal oxide loadings will range from about 0.5 to 25 wt.% of metal oxide based on the total catalyst weight preferably from about 6 to 15 wt.% and still more preferably from about 8 to 12 wt.% metal oxide. The catalyst may also contain minor amounts of other materials that do not adversely affect either the etherification reaction or the stability or regenerability of the catalyst. Included in this category are promoter materials such as barium, calcium and magnesium oxides which, if present, will generally be present in the catalysts in an amount ranging from about 0.1 to 4 wt.%, and preferably from 0.1 to 0.5 wt.% of promoter oxide based on the total catalyst weight.

The catalyst composites used to form the catalysts of this invention may be prepared by any of the well-known techniques such as impregnation, coprecipitation, incipient wetness and the like, the choice being left to the convenience of the practitioner. If impregnation is employed, the support will be impregnated with either an aqueous or an organic solution of a precursor of the desired metal oxide. Aqueous or alcohol solutions such as ethanol solutions, are normally used for convenience. Illustrative, but non-limiting examples of metal salts which may be used in preparing the desired compositions include aqueous solutions of salts such as ammonium metatungstate, as well as nonaqueous solutions of precursors such as $ZrCl_4$, $HfCl_4$, $WCl_6$, $Nb_2(OC_2H_5)_{10}$, $Ta_2(OC_2H_5)_{10}$ and $W(CO)_6$. Additional salts which can be used include soluble bromides, iodides and oxychlorides. Also, organo-metallic metal catalyst precursors such as the cyclic polyolefin carbonyl complexes, or the like, may be employed, i.e., $C_8H_8M(CO)_3$. Acetates and acetylacetonate metal salts, soluble sulfide complexes such as $C_4H_{10}S_2W(CO)_4$ and amine-substituted complexes such as $(pyridine)_3W(CO)_3$ may also be employed. When using the impregnation technique, the impregnating solution will be contacted with the support for a time sufficient to deposit the precursor material onto the support either by selective adsorption or alternatively, the excess solvent may be evaporated during drying, leaving behind the precursor salt. Advantageously, the incipient wetness techniques may be used whereby just enough of a precursor salt solution is added to dampen and fill the pores of the support.

If the catalyst composites are prepared by conventional coprecipitation techniques, a solution of the metal salt or salts will be mixed or comingled with a solution of a soluble salt precursor of the support. Simultaneous precipitation may be induced by pH changes, with the resulting catalyst filtered, dried and calcined in air to convert the metal precursor salt and support precursor salts into oxides.

The composite thus prepared by any of the above recited techniques, or any other known in the art is dried at a temperature of from about 50° to 300° C. to remove the excess solvent and then the transition metal oxide precursors are converted into the oxide form by exposure at temperatures of from 150° to 800° C., preferably 300°-700° C. in an atmosphere such as $O_2$, air, He, Ar, Ne and combinations thereof. Reducing atmospheres may also be used but the resulting composite will require subsequent calcination to convert the reduced metal component to the oxide form. This exposure will be for a time sufficient to convert essentially all of the metal salt precursor to the oxide form. Calcination is useful to decompose the metal salt precursor to the oxide form. Calcination, however, may not be required for certain metal precursor salts which readily convert into metal oxides.

After the catalyst composite comprising one or more transition metal oxides on alumina has been formed, it will be sulfated with a suitable sulfating agent. By sulfating agent is meant $H_2SO_4$, a material which will form $H_2SO_4$ in aqueous solution or which, after being deposited on the surface of the catalyst composite will, upon subsequent calcination, yield sulfate groups on the catalyst surface. Illustrative, but non-limiting examples of suitable sulfating agents include $H_2SO_4$, $(NH_4)_2SO_4$, $SO_3$, etc. with $H_2SO_4$ being particularly preferred. The sulfating may be done in aqueous solution at room temperature. The catalyst composite will be calcined after being treated with the sulfating agent to form the catalyst of this invention. Thus, the sulfated catalyst composite will be calcined in air or other suitable net oxidizing atmosphere at a temperature of at least about 300° C. In a preferred embodiment, the final catalyst will contain at least about 2 wt.% sulfate ions on the surface thereof.

The catalysts useful in the process of this invention are acid catalysts. That is, they have acid properties as determined by either the well-known Hammett Acidity Test which involves titration of a solid acid with n-butyl amine in a non-aqueous solvent followed by addition of a series of Hammett indicators or by the equally well-known Micro Activity Test (MAT) which uses a gas oil feed to determine the cracking activity by converting the gas oil to products boiling in the gasoline range.

The catalysts of this invention may be used to etherify phenol feeds. Such feeds may comprise one or more phenols by themselves or in the presence an inert hydrocarbon. By inert hydrocarbon is meant any hydrocarbon which does not have a deleterious effect on the catalyst or the etherification reaction. The reactant will be selected from the group consisting essentially of aliphatic alcohols, aliphatic ethers and mixtures thereof. If the feed comprises one or more phenols such as phenol, cresols, xylenols, etc., in an inert hydrocarbon such as a raw, phenol-containing, naphtha feed derived from coal liquefaction, the low molecular weight alkyl alcohol and/or ether reactants will preferably have from one to four carbon atoms so as to produce from the phenols ether products which have a boiling point in the naphtha range (i.e., below about 460° F.). In this particular embodiment, methanol is a preferred alcohol reactant and dimethyl ether is a preferred ether reactant.

This invention will further be understood by reference to the examples below.

EXAMPLE 1

In this example, a catalyst was prepared comprising 10 wt.% tungsten oxide and 2.4 wt.% of sulfate ions on a gamma alumina support. Ammonium metatungstate was deposited by impregnation onto a reforming grade of gamma alumina obtained from the Norton Company. The impregnated support was dried over night at 110° C. under vacuum and then calcined in air overnight at 500° C. 10 milliliters of 0.5 M sulfuric acid was added to 20 grams of the calcined catalyst precursor composite. This amount of sulfuric acid was calculated so as to provide 2.4 wt.% sulfate ions to the final catalyst. The 20 grams of the catalyst precursor composite were placed in a round bottom flask after which the 10 milliliters of sulfuric acid was added to the flask, followed by enough water to insure that all of the catalyst precursor was covered with sulfuric acid solution. After one hour, the sulfated catalyst composite was dried under vacuum on a water bath, then in an oven for 65 hours at 140° C., followed by calcining in air for 3 hours at 500° C. An elemental analysis of the catalyst revealed that it contained 0.8 wt.% sulfur (which is equivalent to 2.4 wt.% sulfate ions) and infra red spectra showed a broad shoulder at 1130–1150 cm$^{-1}$ which is characteristic for the sulfate ion. Finally, ESCA analysis revealed 4 wt.% sulfur on the surface of the catalyst.

EXAMPLE 2

In this and in the following examples, a fixed bed quartz reactor was used, the reactor being 30 cm long and having an inside diameter of 1 cm. From about 6 to 8 grams of catalyst were placed in the reactor for each run and a 2/1 molar mixture of methanol/phenol was pumped through the reactor at a rate of 0.25 ml of liquid per minute. This methanol/phenol feed mixture was evaporated into a flowing stream of nitrogen (33.5 ml/min) and passed over the catalyst at a temperature of 205° C. The catalyst was the sulfated catalyst prepared in Example 1. Samples of the gaseous effluent were automatically taken at 30 minute intervals and analyzed by gas-liquid chromatography (GLC) using a 10 ft., 1/8 in. OD column packed with 5% methyl-phenyl silicone SP 2250 on Gaschrom Q (from Supelco Inc.). The selectivity toward anisole production, which is defined as the ratio of anisole produced to the anisole product plus a cresole product, was found to be 0.79.

EXAMPLE 3

This experiment was similar to that of Example 2 except that the catalyst composite was not sulfated. The selectivity towards anisole production calculated as in Example 2 was found to be 0.71.

EXAMPLE 4

This experiment was similar to that of Example 2 with a catalyst prepared using the procedure in Example 1 which comprises 10 wt.% tungsten oxide and 1.2 wt.% sulfate ions on gamma alumina. The selectivity of this catalyst for anisole production was 0.76.

EXAMPLE 5

This experiment was also similar to that of Example 2 using a catalyst prepared as in Example 1 comprising 10 wt.% tungsten oxide and 4.35 wt.% sulfate ions on the gamma alumina. The 4.35 wt.% sulfate ions was obtained by using 20 milliliters of 0.5 M H$_2$SO$_4$ per 20 grams of catalyst precursor composite. The selectivity of this catalyst for anisole production was 0.79.

EXAMPLE 6

This experiment was also similar to that of Example 2, except that the catalyst used was the reforming grade gamm-alumina support on which no tungsten trioxide had been deposited. The selectivity towards anisole production was found to be only 0.65.

EXAMPLE 7

The experiment of Example 6 was repeated, except that the gamma alumina was sulfated as in Example 1 with 2.3% sulfate ions (0.76% sulfur by elemental analysis). The selectivity toward anisole formation was 0.66.

What is claimed is:

1. A catalyst comprising a sulfated composite of an oxide of a transition metal selected from the group consisting essentially of W, Hf, Nb, Ta, Zr and mixtures thereof on a support comprising a high surface area alumina.

2. The catalyst of claim 1 wherein the surface area of said support is at least about 30 M$^2$/g.

3. The catalyst of claim 2 wherein the catlyst contains at least about 0.5% transition metal oxide based on the total catalyst weight.

4. The catalyst of claim 3 wherein said alumina support has a surface area of at least about 50 M$^2$/g.

5. The catalyst of claim 4 wherein the catalyst surface contains at least about 2 wt.% sulfate groups based on the catalyst weight.

6. The catalyst of claim 5 wherein said alumina comprises $\gamma$-Al$_2$O$_3$.

7. The catalyst of claim 6 wherein said metal oxide consists essentially of an oxide of W, Hf and mixtures thereof.

8. A catalyst prepared by sulfating a composite comprising one or more transition metal oxides selected from the group consisting essentially of W, Hf, Nb, Ta, Zr and mixtures thereof supported on a support comprising a high surface area alumina.

9. The catalyst of claim 8 wherein the amount of transition metal oxide is at least about 0.5 wt.% of the total catalyst weight.

10. The catalyst of claim 9 wherein the alumina support has a surface area of at least about 50 M$^2$/g.

11. The catalyst of claim 9 wherein said alumina support comprises gamma alumina.

12. The catalyst of claim 11 wherein said sulfating comprises contacting said catalyst composite with a sulfating agent.

13. The catalyst of claim 12 wherein said catalyst contains at least about 2 wt.% sulfate ions.

14. The catalyst of claim 13 wherein said metal oxide consists essentially of an oxide of W, Hf and mixtures thereof.

15. The catalyst of claim 14 wherein said sulfating is accomplished by contacting said supported transition metal oxide composite with an aqueous solution of H$_2$SO$_4$ followed by calcining the acid treated composite in a net oxidizing atmosphere.

* * * * *